US00PP27887P3

(12) United States Plant Patent
Van Dijk

(10) Patent No.: US PP27,887 P3
(45) Date of Patent: Apr. 11, 2017

(54) ***ANTHURIUM* PLANT NAMED 'ANTHDOSDOH'**

(50) Latin Name: ***Anthurium andreanum* L.**
Varietal Denomination: ANTHDOSDOH

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 65 days.

(21) Appl. No.: 14/545,658

(22) Filed: Jun. 3, 2015

(65) Prior Publication Data

US 2016/0360689 P1 Dec. 8, 2016

(51) Int. Cl.
*A01H 5/02* (2006.01)

(52) U.S. Cl.
USPC ..... Plt./367

(58) Field of Classification Search
USPC ..... Plt./367, 365
See application file for complete search history.

(56) References Cited

PUBLICATIONS

New Plants and Flowers Jan. 30, 2014 Novelties from Dutch *Anthurium* and *phalaenopsis* breeder, retrieved on Sep. 27, 2016, retrieved from the Internet at <http://www.newplantsandflowers.com/novelties-from-dutch-anthurium-and-phalaenopsis-breeder/> 2 pp.*

Upov Pluto Plant Variety Database Sep. 24, 2016, retrieved on Sep. 27, 2016, retrieved from the Internet at <https://www3.wipo.int/pluto/user/en/index.jsp> 1 page.*

EU Community Plant Variety Rights Application No. 2012/2611, Application n°A201201548, filed Nov. 19, 2012, 7 pages.

EU Community Plant Variety Office Official Gazette, Jan. 2013, Feb. 15, 2013, cover page and pp. 27, 44.

www.newplantsandflowers.com/novelties-from-dutch-anthurium-and-phalaenopsis-breeder/, published Jan. 30, 2014, 2 pages, retrieved from the internet on Dec. 12, 2016.

EU Community Plant Variety Rights Grant No. EU 38413, issued Jun. 16, 2014, 2 pages.

* cited by examiner

*Primary Examiner* — June Hwu

(74) *Attorney, Agent, or Firm* — Jondle & Associates, P.C.

(57) ABSTRACT

A new and distinct variety of *Anthurium* plant named 'ANTHDOSDOH' particularly characterized by having a pink, lanceolate spathe, a purple spadix with a red tip, a lanceolate leaf, an extremely compact plant habit and light green foliage is disclosed.

3 Drawing Sheets

Genus and species: *Anthurium andreanum* L.
Variety denomination: 'ANTHDOSDOH'.

BACKGROUND OF THE NEW PLANT

The present invention comprises a new and distinct variety of *Anthurium*, botanically known as *Anthurium andreanum* L., and hereinafter referred to by the variety name 'ANTHDOSDOH'. The new variety originated from a hybridization made in September 2006 in Bleiswijk, The Netherlands. The female parent is a light pink *Anthurium* pot plant designated '9941-01' (unpatented), and the male parent was a pink *Anthurium* plant designated '9741-04' (unpatented).

A single plant was selected in June 2008 and has been asexually reproduced repeatedly by meristem tissue culture in Bleiswijk, The Netherlands over a seven-year period. The present invention has been found to retain its distinctive characteristics through successive asexual propagations.

Plant Breeder's Rights for this variety have been applied for in the European Union on Nov. 19, 2012, in Japan on May 26, 2014 and in Vietnam on Nov. 26, 2014. 'ANTHDOSDOH' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Pink, lanceolate spathe;
2) Purple spadix with red tip;
3) Lanceolate leaf;
4) Extremely compact plant habit; and
5) Light green foliage.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 50-week old plant grown in a greenhouse in Bleiswijk, The Netherlands in 2014.

DESCRIPTION OF THE NEW VARIETY

Figure 1:
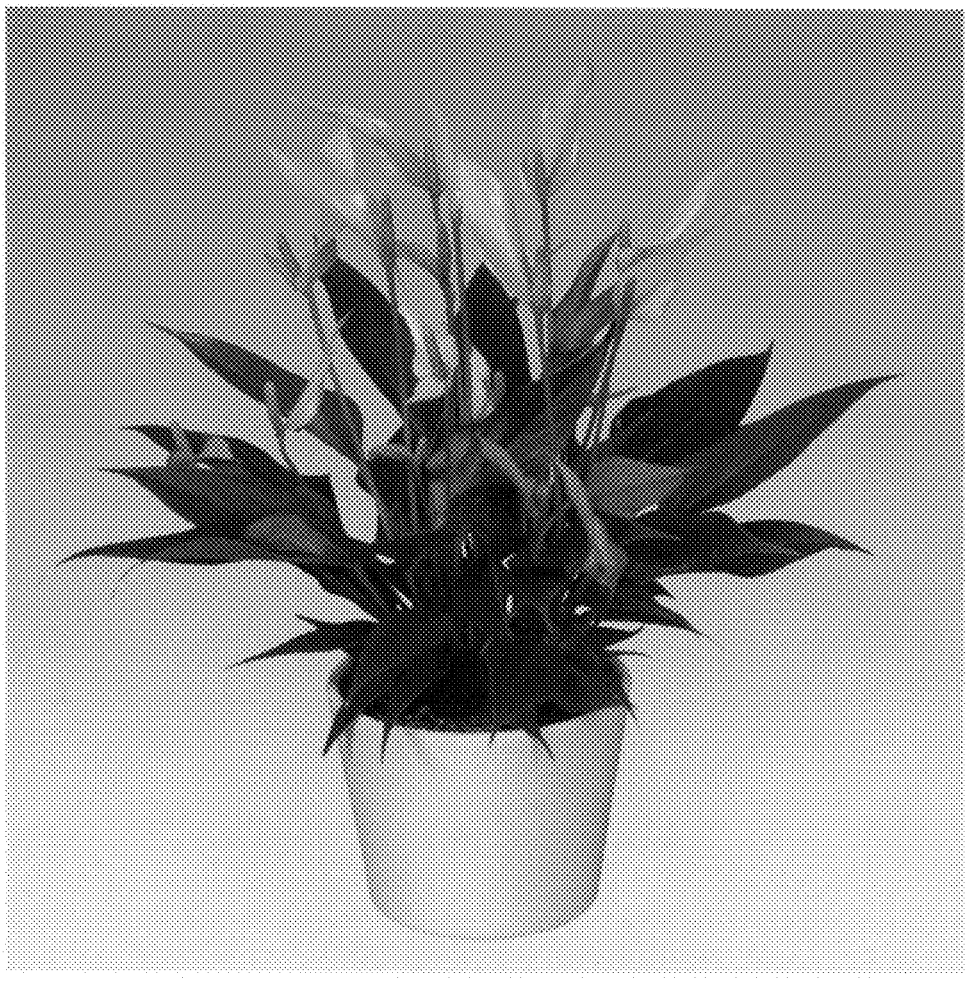
FIG. 1 shows the overall plant habit, including blooms and foliage.
Figure 2:
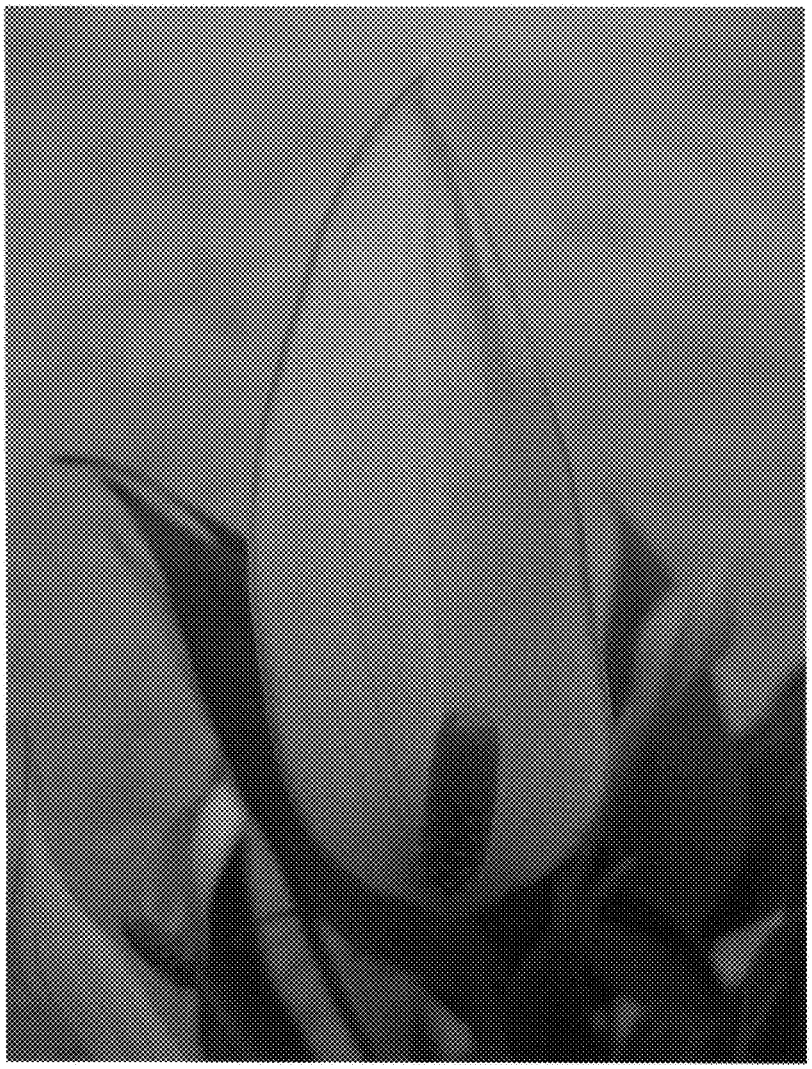
FIG. 2 shows a close-up of the mature spathe.
Figure 3:
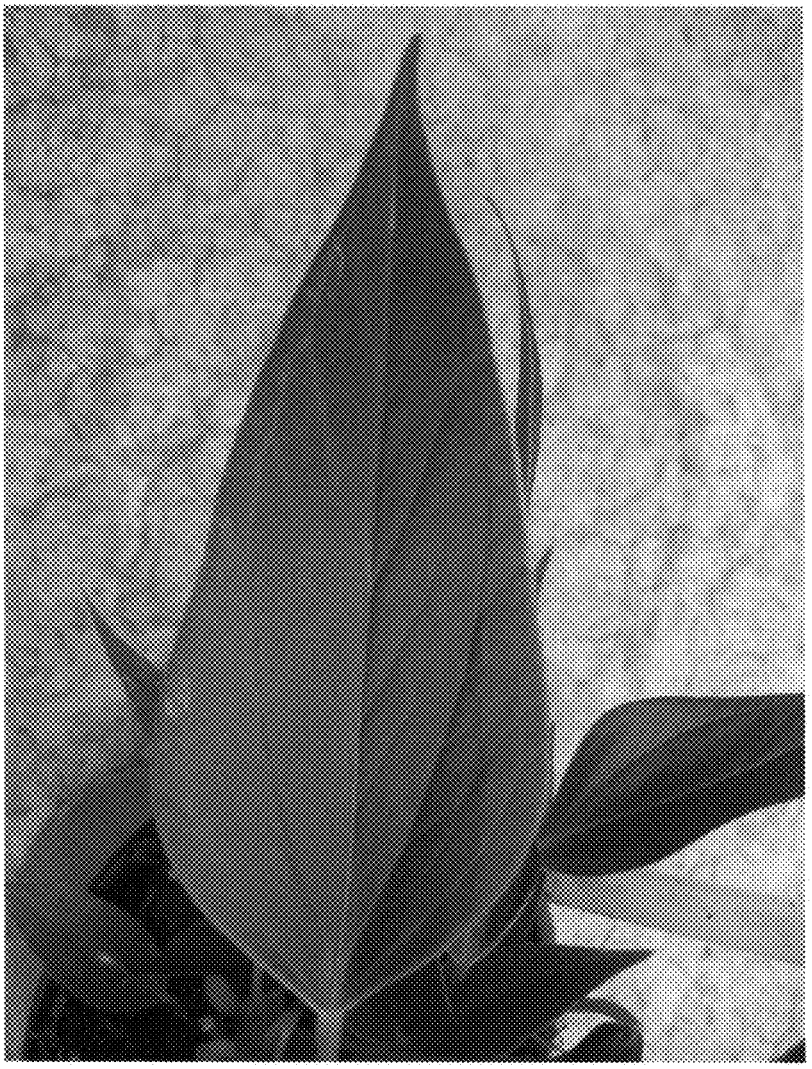
FIG. 3 shows the upper leaf blade surface.

The following detailed description sets forth the distinctive characteristics of 'ANTHDOSDOH'. The data which define these characteristics were collected from asexual reproductions carried out in Bleiswijk, The Netherlands. The plant history was taken on 50-week old plants which were planted from tissue culture in 12-centimeter pots and grown in a glass greenhouse between 19° C. and 24° C. Observations were made in April 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDOSDOH'.

Parentage:

*Female parent*.—*Anthurium* plant '9941-01' (unpatented).

*Male parent*.—*Anthurium* plant '9741-04' (unpatented).

Plant:

*Propagation*.—Tissue culture.

*Root description*.—Fleshy white-cream colored roots with small hairy lateral roots having yellow-colored root tips.

*Time to produce a finished flowering plant*.—25 to 30 weeks for a 12 cm pot.

*Growth habit*.—Herbaceous perennial.

*Height* (*measured from soil, including inflorescence*). —20.0 cm to 24.0 cm.

*Width* (*measured from leaf tips*).—25.0 cm to 30.0 cm.

Leaves:

*Immature leaves*.—Length: 5.0 cm to 9.0 cm. Width: 2.0 cm to 4.0 cm. Color: Upper surface: RHS 144A. Lower surface: RHS 144B. Texture (both upper and lower surfaces): Shiny.

*Mature leaves*.—Length (fully expanded): 9.0 cm to 13.0 cm. Width: 3.0 cm to 5.0 cm. Shape: Lanceolate. Apex: Acuminate. Base: Cuneate. Leaf blade angle with the petiole: Between 140 degrees and 160 degrees. Leaf margin: Entire. Color: Upper surface: RHS 137A. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Not present.

*Petiole*.—Cross-section: Round. Diameter: 0.2 cm to 0.3 cm. Length: 4.0 cm to 8.0 cm for a mature leaf size. Color: Mature leaf: RHS 146C. Immature leaf: RHS 146C. Cataphyll color surrounding the petiole: Outside: RHS 144A. Inside: RHS 144A.

*Geniculum*.—Length: 0.8 cm to 1.0 cm. Width: 0.3 cm to 0.4 cm. Color: RHS 146C.

Inflorescence:

*Arrangement*.—Single.

*Flowering habit* (*length of flowering season*).—Continuous.

*Number of inflorescences per plant*.—7 to 10.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 130 degrees and 150 degrees; the spathe stands on a wiry peduncle about 5.0 cm to 7.0 cm above the foliage.

*Shape*.—Lanceolate.

*Apex*.—Acuminate.

*Base*.—Rotundate.

*Texture*.—Shiny and smooth.

*Margin*.—Entire.

*Size*.—Length: 6.0 cm to 7.0 cm. Width: 2.0 cm to 3.0 cm.

*Color*.—Just fully open: Upper surface: RHS 54A. Lower surface: RHS 54C. Fading spathe: Upper surface: Light green (RHS 146D) and light pink (RHS 51D). Lower surface: Light pink (RHS 51D) and light green (RHS 146B). After opening, the spathe slowly starts fading from pink to light pink.

Peduncle:

*Shape*.—Erect.

*Cross-section*.—Round.

*Length*.—12.0 cm to 15.0 cm.

*Diameter*.—0.2 cm to 0.3 cm.

*Color*.—RHS 152B.

Flowering time:

*General*.—One small rooted untreated tissue culture plant of 2.0 cm tall will flower after 3 to 4 months, depending on the season, and 4 to 6 blossoms will appear. More blossoms appear after some additional weeks so that a full flowering and commercial plant will have 7 to 10 pink spathes. Smaller blossoms may occur on less mature plants.

Spadix:

*Size*.—Length: 1.5 cm to 2.5 cm (depending on flower size). Width (at apex): 0.35 cm to 0.45cm. Width (at base): 0.4 cm to 0.5 cm.

*Shape*.—Columnar.

*Angle from spadix tip to peduncle*.—160 to 180 degrees (spadix is almost in one line with the peduncle).

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 47A. Mature: RHS 61A. Fading: Red-purple (RHS 183D).

Flowers:

*Quantity per spadix*.—90 to 110.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 61A.

Reproductive organs:

*Stamens*.—Not visible.

*Pollen amount*.—Very few.

*Pollen color*.—RHS 156D.

*Pistil*.—Quantity: Many. Length: Less than 0.01 cm. Color: RHS 61C.

*Style*.—Not observed.

*Stigma*.—Shape: Ovoid. Diameter: Less than 0.01 cm. Color: RHS 61C.

*Ovary*.—Rarely visible.

*Ovary color*.—Not measured.

Fruit and seed set: None observed.

Disease and pest resistance: Not observed to date.

COMPARISON WITH PARENTAL AND COMMERCIAL VARIETIES

'ANTHDOSDOH' differs from the female parent plant '9941-01' (unpatented) in that 'ANTHDOSDOH' has a pink spathe, whereas '9941-01' has a light pink spathe.

'ANTHDOSDOH' differs from male parent plant '9741-04' (unpatented) in that 'ANTHDOSDOH' has a lanceolate spathe, whereas '9741-04' has an ovate spathe.

'ANTHDOSDOH' differs from commercial variety 'ANTHUCOEN' (U.S. Plant Pat. No. 22,630) in that 'ANTHDOSDOH' has a small, lanceolate spathe, whereas 'ANTHUCOEN' has a larger, more ovate spathe. Additionally, 'ANTHDOSDOH' has lanceolate leaves, whereas 'ANTHUCOEN' has cordate leaves.

'ANTHDOSDOH' differs from commercial variety 'ANTHEBENEX' (unpatented) in that 'ANTHDOSDOH' has a pink spathe, whereas 'ANTHEBENEX' has a purple spathe. Additionally, 'ANTHDOSDOH' has small, lanceolate leaves, whereas 'ANTHEBENEX' has larger, long ovate leaves.

I claim:

1. A new and distinct variety of *Anthurium* plant named 'ANTHDOSDOH', substantially as illustrated and described herein.

* * * * *